United States Patent
Seeley et al.

(10) Patent No.: US 9,962,552 B2
(45) Date of Patent: May 8, 2018

(54) IMPLANTABLE MEDICAL DEVICE WITH SWAPPABLE HEADERS

(75) Inventors: Dale F. Seeley, Spring Park, MN (US); Jason D. Rahn, Andover, MN (US); Michael T. Hegland, Mounds View, MN (US); Carl D. Wahlstrand, North Oaks, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 639 days.

(21) Appl. No.: 13/299,063

(22) Filed: Nov. 17, 2011

(65) Prior Publication Data

US 2012/0130438 A1 May 24, 2012

Related U.S. Application Data

(60) Provisional application No. 61/415,069, filed on Nov. 18, 2010.

(51) Int. Cl.
| | |
|---|---|
| *A61N 1/37* | (2006.01) |
| *A61N 1/375* | (2006.01) |
| *H01R 24/76* | (2011.01) |
| *H01R 24/00* | (2011.01) |
| *H01R 107/00* | (2006.01) |

(52) U.S. Cl.
CPC ........... *A61N 1/3752* (2013.01); *H01R 24/76* (2013.01); *A61N 1/3754* (2013.01); *H01R 24/00* (2013.01); *H01R 2107/00* (2013.01); *Y10T 29/49169* (2015.01)

(58) Field of Classification Search
CPC ... A61B 5/02141; A61N 1/375; A61N 1/3968
USPC ..................................................... 607/36–38
See application file for complete search history.

(56) References Cited

U.S. PATENT DOCUMENTS

| | | | |
|---|---|---|---|
| 5,383,913 A | | 1/1995 | Schiff |
| 5,679,026 A | * | 10/1997 | Fain et al. ............... 607/37 |
| 5,899,930 A | | 5/1999 | Flynn |

(Continued)

FOREIGN PATENT DOCUMENTS

| | | |
|---|---|---|
| EP | 2 153 868 | 2/2010 |
| WO | WO 2008/025159 | 3/2008 |

(Continued)

OTHER PUBLICATIONS

PCT/US2011/061208, Invitation to Pay Additional Fees with Partial Search Report dated May 3, 2012.

(Continued)

*Primary Examiner* — Michael Carey
*Assistant Examiner* — Natasha Patel
(74) *Attorney, Agent, or Firm* — Mueting, Raasch & Gebhardt, P.A.

(57) ABSTRACT

An implantable electrical medical device system includes a device body portion having a plurality of contacts operably coupled to discrete channels of electronics. One or more swappable headers may be attached to the device body portion by an end user, such as an implanting physician, to operably couple internal lead receptacle contacts in the header to the contacts of the device body portion. The swappable headers may have lead receptacles configured to receive differing types or combinations of leads, allowing an end user to select one or more appropriate headers as desired.

10 Claims, 11 Drawing Sheets

(56) References Cited

U.S. PATENT DOCUMENTS

| | | | |
|---|---|---|---|
| 6,321,126 B1* | 11/2001 | Kuzma | 607/137 |
| 7,031,774 B1 | 4/2006 | Doan | |
| 7,083,474 B1 | 8/2006 | Fleck et al. | |
| 7,376,465 B2 | 5/2008 | Hornfeldt | |
| 7,515,964 B1* | 4/2009 | Alexander | A61N 1/3752 |
| | | | 607/36 |
| 7,537,474 B2 | 5/2009 | Deininger et al. | |
| 7,563,141 B2 | 7/2009 | Alexander | |
| 7,702,385 B2 | 4/2010 | Moffitt | |
| 7,856,272 B2 | 12/2010 | Nikitin | |
| 8,934,973 B2 | 1/2015 | Wahlstrand et al. | |
| 2003/0171783 A1* | 9/2003 | Tsukamoto et al. | 607/36 |
| 2004/0106964 A1 | 6/2004 | Fischer | |
| 2006/0167522 A1* | 7/2006 | Malinowski | A61N 1/3752 |
| | | | 607/37 |
| 2006/0224208 A1 | 10/2006 | Naviaux | |
| 2007/0111587 A1 | 5/2007 | Ries | |
| 2008/0015668 A1* | 1/2008 | Soukup | 607/115 |
| 2009/0017668 A1* | 1/2009 | Deininger | H01R 12/592 |
| | | | 439/346 |
| 2009/0018601 A1* | 1/2009 | Deininger et al. | 607/37 |
| 2010/0137929 A1 | 6/2010 | Libbey et al. | |
| 2010/0274309 A1 | 10/2010 | Knipfer | |
| 2012/0083867 A1 | 4/2012 | Wahlstrand et al. | |
| 2012/0130437 A1 | 5/2012 | Seeley | |

FOREIGN PATENT DOCUMENTS

| | | |
|---|---|---|
| WO | WO 2010/148379 | 12/2010 |
| WO | WO 2011/002913 | 1/2011 |
| WO | WO 2012/027126 | 3/2012 |
| WO | WO 2012/068325 A1 | 5/2012 |

OTHER PUBLICATIONS

PCT/US2011/061208 Search Report and Written Opinion dated Sep. 12, 2012.

PCT/US2011/061114; International Preliminary Examination Report dated May 21, 2013. 8 pages.

PCT/US2011/061114; International Search Report and Written Opinion dated May 3, 2012. 11 pages.

PCT/US2011/061208; International Preliminary Report on Patentability, dated May 30, 2013, 11 pages.

\* cited by examiner

# IMPLANTABLE MEDICAL DEVICE WITH SWAPPABLE HEADERS

RELATED APPLICATION

This application claims the benefit of priority to U.S. Provisional Application No. 61/415,069, filed on Nov. 18, 2010, which application is hereby incorporated by reference in its entirety to the extent that it does not conflict with the disclosure presented herein.

FIELD

This application relates to implantable medical devices; more particularly to systems and devices that include an implantable electrical medical device, such as an electrical signal generating device or monitoring device.

BACKGROUND

Implantable electrical signal generators have been used to treat a variety of diseases and have been used in a variety of manners. For example, deep brain stimulation has been used to treat Parkinson's disease and essential tremor, and spinal cord stimulation or peripheral nerve stimulation has been used to treat pain. Implantable medical leads are operably coupled to the signal generators and carry electrical signals to appropriate locations of the patient so that a therapeutic benefit may be obtained.

A variety of different implantable leads may be selected for use in such therapies. However, currently available implantable signal generators are configured to be coupled to leads of a given type. For example, an implantable electrical signal generator may be configured to receive one or two eight electrode leads. To use four electrode leads with such a device, an adaptor or bifurcating lead extension may be employed.

In the past electrical signal generators, such as neurostimulators, were generally limited to 8 or 16 channels (e.g., capable of providing independent electrical signals to only eight or 16 electrodes). However, with technological advancement, implantable signal generators may have significantly more channels, such as 32 or 64, which allows for more electrodes to be used in therapy. Yet, such signal generators are still configured to accept only particular types of leads, unless an adaptor or the like is used.

BRIEF SUMMARY

The present disclosure describes, among other things, implantable electrical medical devices, such as signal generators, and systems that may be simultaneously operably coupled to a variety of types of leads, such as four electrode leads and eight electrode leads. The devices are configured to receive more than one connector header. The connector headers may be configured to receive different types or configurations of leads.

Accordingly, a physician may readily employ more than one type of lead with a single implantable signal generator. This may provide the physician with the ability to employ more flexible treatment strategies for a particular disease or to provide a variety of therapies, such as spinal cord stimulation and subcutaneous stimulation, at the same time. In addition or alternatively, the physician may no longer need to select from a variety of makes and models of implantable electrical medical devices depending on the therapeutic needs of the patient, but rather may use a single device in a variety of situations.

In embodiments, an implantable electrical medical system includes a device body portion and a connector header. The device body portion comprises (i) a hermetically sealed housing; (ii) electronics disposed in the housing and configured to generate or receive an electrical signal, the electronics containing a plurality of channels through which the electrical signal may be transmitted; (iii) a plurality of feedthroughs extending through the hermetically sealed housing, wherein each feedthrough is operably coupled to a discrete channel of the electronics; and (iv) a plurality of device contacts electrically coupled to the feedthroughs, wherein each device contact is electrically coupled to a discrete feedthrough. The connector header portion comprises (i) a housing defining a bore; (ii) a lead receptacle within the bore of the housing; the lead receptacle comprising a plurality of receptacle contacts operably couplable to a lead inserted into the receptacle; and (iii) a plurality of header contacts electrically coupled to the receptacle contacts. Each of the header contacts is electrically coupled to a discrete receptacle contact. The connector header portion is removable and attachable to the device body portion such that, when attached, the header contacts and the device contacts electrically couple.

In embodiments, an implantable electrical medical system includes a device body portion, and first and second connector header portions. The device body portion comprises (i) a hermetically sealed housing; (ii) electronics disposed in the housing and configured to generate or receive an electrical signal, the electronics containing a plurality of channels through which the electrical signal may be transmitted; (iii) a first set of a plurality of feedthroughs extending through the hermetically sealed housing, wherein each feedthrough is operably coupled to a discrete channel of the electronics; (iv) a second set of a plurality of feedthroughs extending through the hermetically sealed housing, wherein each feedthrough is operably coupled to a discrete channel of the electronics; (v) a first set of a plurality of device contacts electrically coupled to the first set of feedthroughs, wherein each device contact is electrically coupled to a discrete feedthrough; and (vi) a second set of a plurality of device contacts electrically coupled to the second set of feedthroughs, wherein each device contact is electrically coupled to a discrete feedthrough. The first connector header portion comprises (i) a housing defining a bore; (ii) a lead receptacle within the bore of the housing; the lead receptacle comprising a plurality of receptacle contacts operably couplable to a lead inserted into the receptacle; and (iii) a plurality of header contacts electrically coupled to the receptacle contacts, wherein each of the header contacts is electrically coupled to a discrete receptacle contact. The first connector header portion is removable and attachable to the device body portion such that, when attached, the first header contacts and the first set of device contacts electrically couple. The second connector header portion comprises (i) a housing defining a bore; (ii) a lead receptacle within the bore of the housing; the lead receptacle comprising a plurality of receptacle contacts operably couplable to a lead inserted into the receptacle; and (iii) a plurality of second header contacts electrically coupled to the receptacle contacts, wherein each of the header contacts is electrically coupled to a discrete receptacle contact. The second connector header portion is removable and attachable to the device body portion such that, when attached, the second header contacts and the second set of device contacts electrically couple.

In embodiments, a method for manufacturing a device body portion of an implantable medical device is described. The device body portion is configured to receive a plurality of connector header portions. The method includes providing a device body portion having a hermetically sealed housing, electronics disposed in the housing and having a plurality of channels through which electrical signals may be transmitted and a plurality of feedthroughs extending through the hermetically sealed housing, wherein each feedthrough is operably coupled to a discrete channel of the electronics. The method further includes welding a frame on the housing of the device body portion over the feedthroughs, wherein the frame has a side window through which the feedthroughs are accessible. The method also includes electrically coupling contact pads to the feedthroughs such that each contact pad is discretely coupled to a feedthrough. The method additionally includes filling the side window of the frame with an electrically insulating polymer.

In embodiments, an implantable electrical medical device is configured to be coupleable to a swappable header configured (i) to receive one or more leads and (ii) to operably couple the leads to the device. The implantable electrical medical device comprises (a) a hermetically sealed housing; (b) electronics disposed in the housing and configured to generate or receive an electrical signal, the electronics containing a plurality of channels through which the electrical signal may be transmitted; (c) a plurality of feedthroughs extending through the hermetically sealed housing, wherein each feedthrough is operably coupled to a discrete channel of the electronics; and (d) a plurality of contacts electrically coupled to the feedthroughs, wherein each contact is electrically coupled to a discrete feedthrough. The contacts are positioned such that proper alignment and attachment of the swappable header to the device causes the contacts to be electrically coupled to corresponding contacts of the header such that leads inserted into the header may be operably coupled to the electronics of the device via the contacts of the header, the contacts of the device, and the feedthroughs.

One or more embodiments of the devices, systems or methods described herein may provide one or more advantages over existing systems, devices and methods. One of skill in the art will appreciate the advantages provided upon reading the description that follows.

Figure 1:
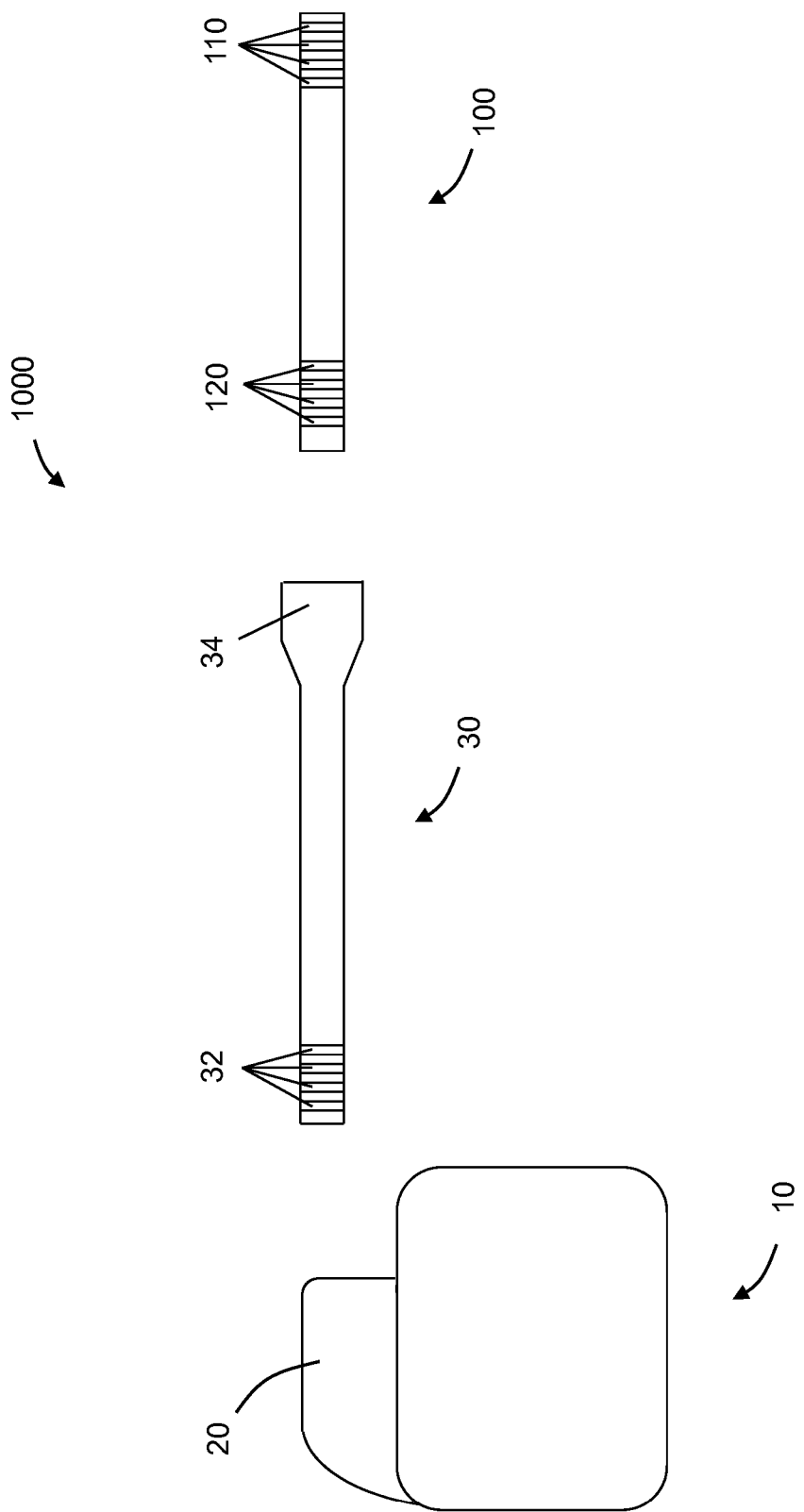
FIG. 1 is a schematic side view of an implantable system including an implantable electrical medical device, a lead extension and a lead.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not necessarily intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content and context clearly dictates otherwise.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising."

Any direction referred to herein, such as "top," "bottom," "left," "right," "upper," "lower," "above," below," and other directions and orientations are described herein for clarity in reference to the figures and are not to be limiting of an actual device or system or use of the device or system. Devices or systems as described herein may be used in a number of directions and orientations.

The present disclosure, among other things relates to, among other things, electrical medical devices, such as electrical signal generators or monitoring devices, and systems that may employ multiple medical leads. The systems and devices described herein may provide for flexibility in the number and types of leads that may be operably coupled to an implantable electrical medical device. The leads may be signal emitting leads or sensing leads.

Nearly any implantable medical device or system employing leads may be used in conjunction with the leads, extensions or adaptors described herein. Representative examples of such implantable medical devices include hearing implants, cochlear implants; sensing or monitoring devices; signal generators such as cardiac pacemakers or defibrillators, neurostimulators (such as spinal cord stimulators, brain or deep brain stimulators, peripheral nerve stimulators, vagal nerve stimulators, occipital nerve stimulators, subcutaneous stimulators, etc.), gastric stimulators; or the like.

Referring to FIG. 1, a side view of a schematic implantable system 1000 is shown. In the depicted system 1000, the implantable electrical medical device 10 includes a connector header 20 configured to receive a proximal portion of lead extension 30. The proximal portion of lead extension 30 contains a plurality of electrical contacts 32 that are electrically coupled to internal contacts (not shown) at distal connector 34 of lead extension 30. The connector header 20 of the signal generator 10 contains internal contacts (not shown) and is configured to receive the proximal portion of the lead extension 30 such that the internal contacts of the connector header 20 may be electrically coupled to the contacts 32 of the lead extension 30 when the lead extension 30 is inserted into the header 20.

The system depicted in FIG. 1 further includes a lead 100. The depicted lead 100 has a proximal portion that includes a plurality of contacts 120 and a distal portion that includes a plurality of electrodes 110. Each of the electrodes 110 may be electrically coupled to a discrete contact 120. The distal connector 34 of the lead extension 30 is configured to receive the proximal portion of the lead 100 such that the contacts 120 of the lead 100 may be electrically coupled to the internal contacts of the connector 34 of the extension 30. Accordingly, a signal generated by the implantable electrical device 10 may be transmitted to a tissue of a patient by an electrode 110 of lead 100 when lead is connected to extension 30 and extension 30 is connected to implantable electrical device 10. Alternatively or in addition, a signal received by electrode 110 of lead 100 from a patient may be transmitted to a contact of the device 10 when lead is connected to extension 30 and extension 30 is connected to the device 10.

It will be understood that lead 100 may be coupled to implantable medical device 10 without use of an extension 30. Any number of leads 100 or extensions 20 may be coupled to device 10. While lead 100 is depicted as having four electrodes 110, it will be understood that lead 100 may include any number of electrodes 110, e.g. one, two, three, four, five, six, seven, eight, sixteen, thirty-two, or sixty-four. Corresponding changes in the number of contacts 120 in lead 100, contacts 32 and internal contacts in connector 34 of lead extension, or internal contacts in connector 20 of device 10 may be required or desired.

As used hereinafter, "lead" will refer to both "leads" and "lead extensions" unless the content and context clearly dictates otherwise.

Figure 2A:
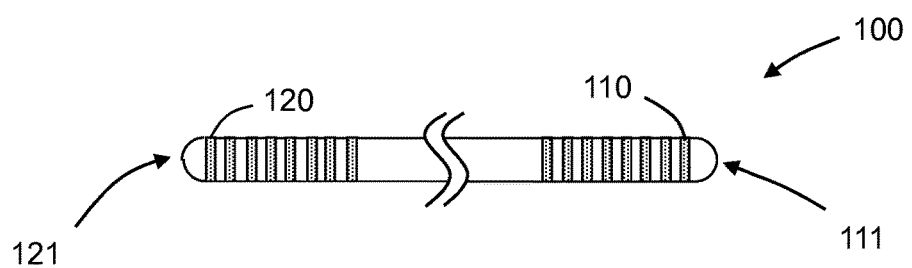
FIGS. 2A-2B are schematic side views of implantable medical leads.
Figure 2B:
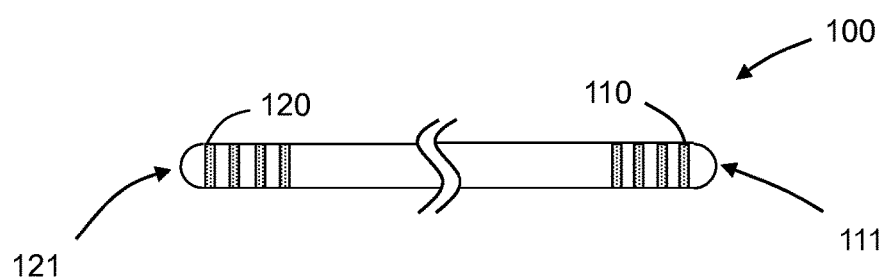

Referring now to FIGS. 2A-B, schematic side views of leads 100 are shown. The leads 100 have a proximal end 121 and a distal end 111. A plurality of contacts 120 are disposed in proximity to the proximal end 121 of the lead 100, and a plurality of electrodes 110 are disposed in proximity to the distal end 111 of the lead 100. Typically, each contact 120 is electrically coupled to a discrete electrode 110, such as through an insulated conductive wire running within the body of the lead. The proximal end 121 of the lead is insertable into a receptacle of an implantable electrical medical device such that the contacts 120 of the lead 100 may be electrically coupled with internal contacts of the receptacle.

The lead depicted in FIG. 2A has eight contacts 120 and eight electrodes 110, while the lead depicted in FIG. 2B has four contacts 120 and four electrodes 110. The pitch, i.e. space between contacts 120, is different between the four (1B) and eight (1A) electrode leads, which is typical of such leads. In the depicted eight electrode 110 lead (1A) the contacts 120 are closer to each other than in the depicted four electrode 110 lead (1B).

Figure 3A:
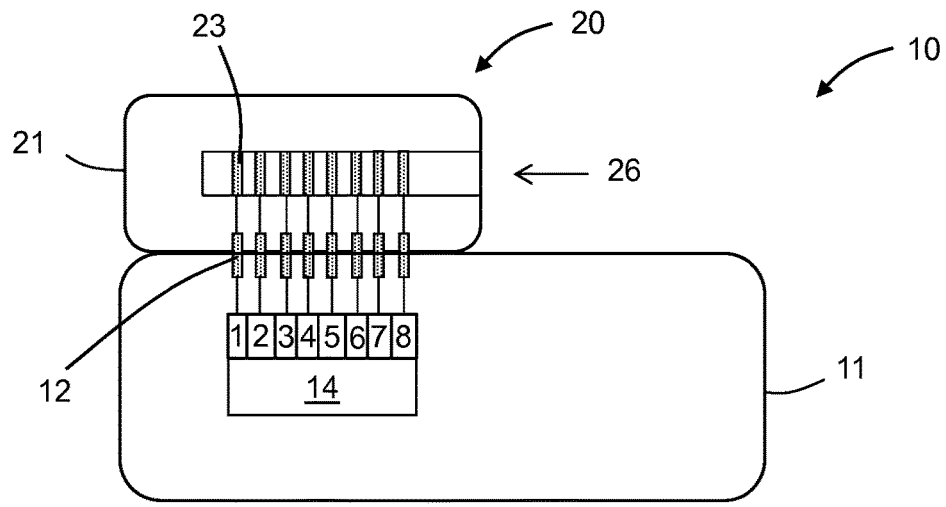
FIGS. 3A-B are schematic sectional views of implantable electrical medical devices showing feedthroughs coupled to contacts of a lead receptacle of the device.
Figure 3B:
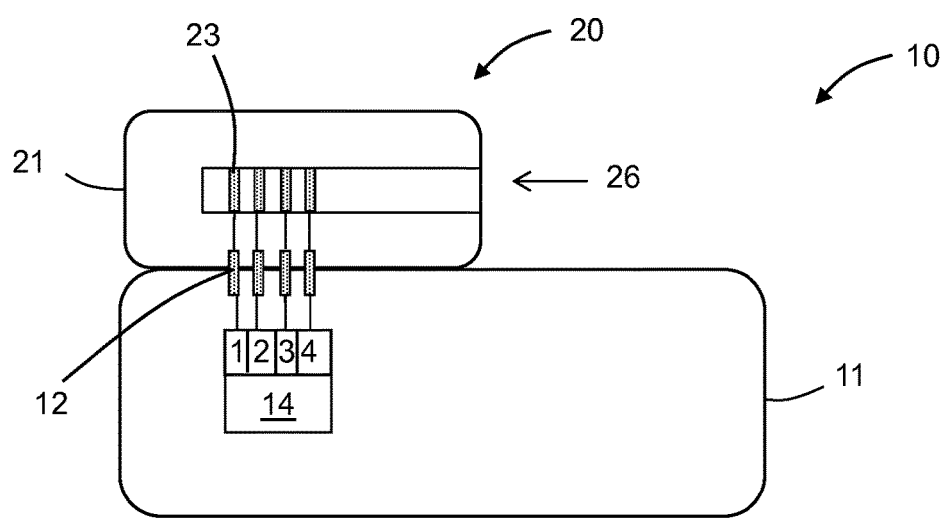

Referring now to FIGS. 3A-B, schematic sectional side views of implantable electrical medical devices 10 are shown. The devices 10 depicted in FIGS. 3A and 3B, respectively, are configured to receive and operably couple to the leads 100 depicted in FIGS. 2A and 2B, respectively. The devices 10 depicted in FIGS. 3A-B include a hermetically sealed housing 11 in which electronics 14 are disposed, and a connector header 20 disposed on the device housing 11. A lead receptacle 26 is formed in the housing 21 of the header 20. The receptacle 26 is configured to receive and electrically couple to contacts of a lead.

The receptacle 26 has internal contacts 23 positioned to align with and electrically couple with contacts of a lead when the lead is properly inserted into the receptacle. The pitch, or spacing of, internal contacts 23 of the receptacle 26 depicted in FIG. 3A is different from the pitch of the internal contacts 23 depicted in FIG. 3B. The pitch of the internal contacts 23 of FIG. 3A is configured to allow electrical connection between the contacts 121 of a lead as depicted in FIG. 2A. The pitch of the internal contacts 23 of FIG. 3B is configured to allow electrical connection between the contacts 121 of a lead as depicted in FIG. 2B. Implantable electrical devices, according to embodiments described herein in more detail below, may have headers with multiple lead receptacles with different receptacles configured to be coupled to different leads, such as leads having four, eight, sixteen, or any number of electrodes or leads having the same number of electrodes with different pitches or spacing between proximal contacts of the leads.

Still referring to FIGS. 3A-B, electronics 14 are configured to send electrical signals to tissue of a patient, or receive signals from a tissue of a patient, through leads operably coupled to electronics 14 of the device 10 As used herein, the term "transmitted electrical signals" is used to refer to both the signals sent by electronics 14 to tissue of the patient or received by electronics 14 from the tissue of the patient. As depicted, channels 1-8, 1-4 of the electronics 14 are discretely coupled to internal contacts 23 of lead receptacles 26 via feedthroughs 12, which extend through hermetically sealed housing 11. As used herein, a "channel" of the electronics is a discrete electronic pathway through which signals may be transmitted independently of another channel. The feedthroughs 12 may be electrically coupled with internal contacts 23 via welding, soldering, brazing, coupling via conductive wires, or the like. Each channel of the electronics 14 can be independently coupled with a discrete internal contact 23 of a receptacle, which can be coupled with a discrete contact of a lead, which can be coupled with a discrete electrode of the lead. Accordingly, each channel of the electronics 14 may be operably coupled to a given electrode of a lead.

One problem with existing implantable electrical devices is that they are generally configured to receive only one type of lead, e.g., a four electrode (quad) lead or an eight electrode (octad) lead. In embodiments, the devices described herein have multiple receptacles, some of which are configured to receive and operably couple to, for example, an octad electrode lead and some of some of which are configured to receive and operably couple to, for example, an quad lead.

Figure 4A:
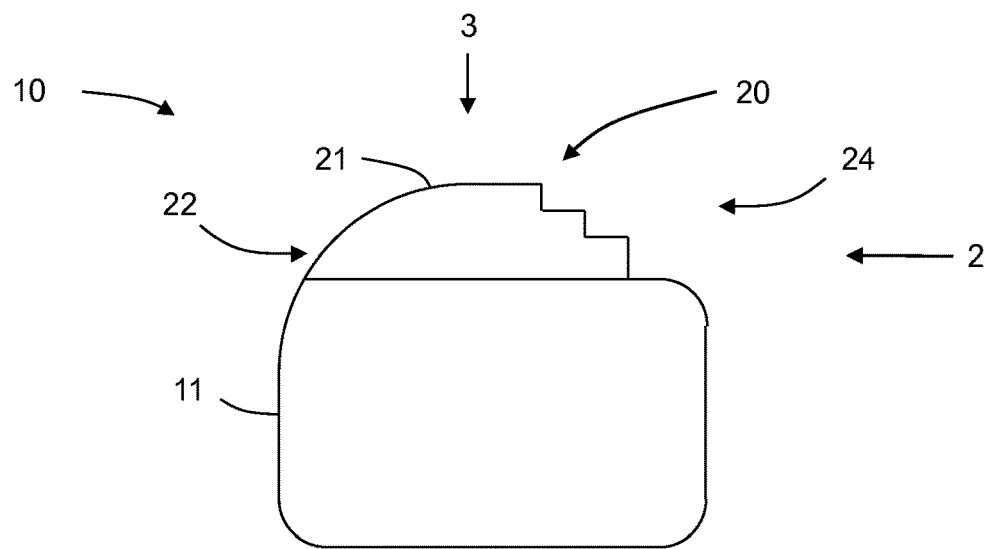
FIG. 4A is a schematic side view of an embodiment of an implantable electrical medical device.
Figure 4B:
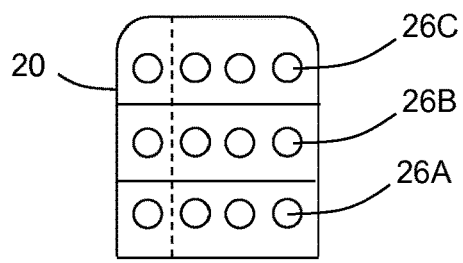
FIGS. 4B-C are schematic front (B) and top (C) views of an embodiment of the implantable electrical medical device shown in FIG. 4A.
Figure 4C:
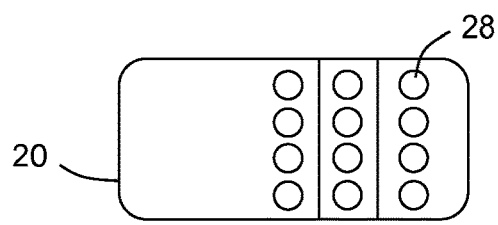

By way of example and with reference to FIGS. 4A-C, schematic side, front, and top views of implantable electrical device 10 or header 20 are shown. The connector header 20 has 12 bores or receptacles with a top row of four receptacles 26C, a middle row of four receptacles 26B, and a bottom row of four receptacles 26A. The front face 24 of the upper row of receptacles 26C is offset towards the back 22 of the header 20 relative to the middle row of receptacles 26B. The front face 24 of the middle row of receptacles 26B is offset towards the back 22 of the header 20 relative to the lower row of receptacles 26A. In this manner, set screws 28 (see FIG. 4C) are accessible from the top of the header 20. Each receptacle 26A, 26B, 26C has a corresponding set screw 28 tightenable relative to the header housing 21 for securing a lead within the respective receptacle. Of course any mechanism other than a set screw for securing a lead within a receptacle may be used.

In the embodiment depicted in FIGS. 4A-B, leads may be first inserted into the lower receptacles 26A and the appropriate set screws tightened prior to insertion of leads into the middle receptacles 26B (as insertion of leads into the middle receptacles may interfere with the ability to tighten the set screws of the lower receptacles). Similarly, leads may be first inserted into the middle receptacles 26B and the appropriate set screws tightened prior to insertion of leads into the upper receptacles 26C.

The implantable electrical medical device 10 depicted in FIGS. 4A-C may have any suitable number of channels, such as 64 channel or 32 channels. By way of example, the lower set of four receptacles 26A may each have eight internal contacts, while each of the middle 26B and upper 26C receptacle may have four internal contacts. Accordingly, the device 10 may allow for operable connection of a variety of types of leads without the use of adaptors or the like.

Figure 5:
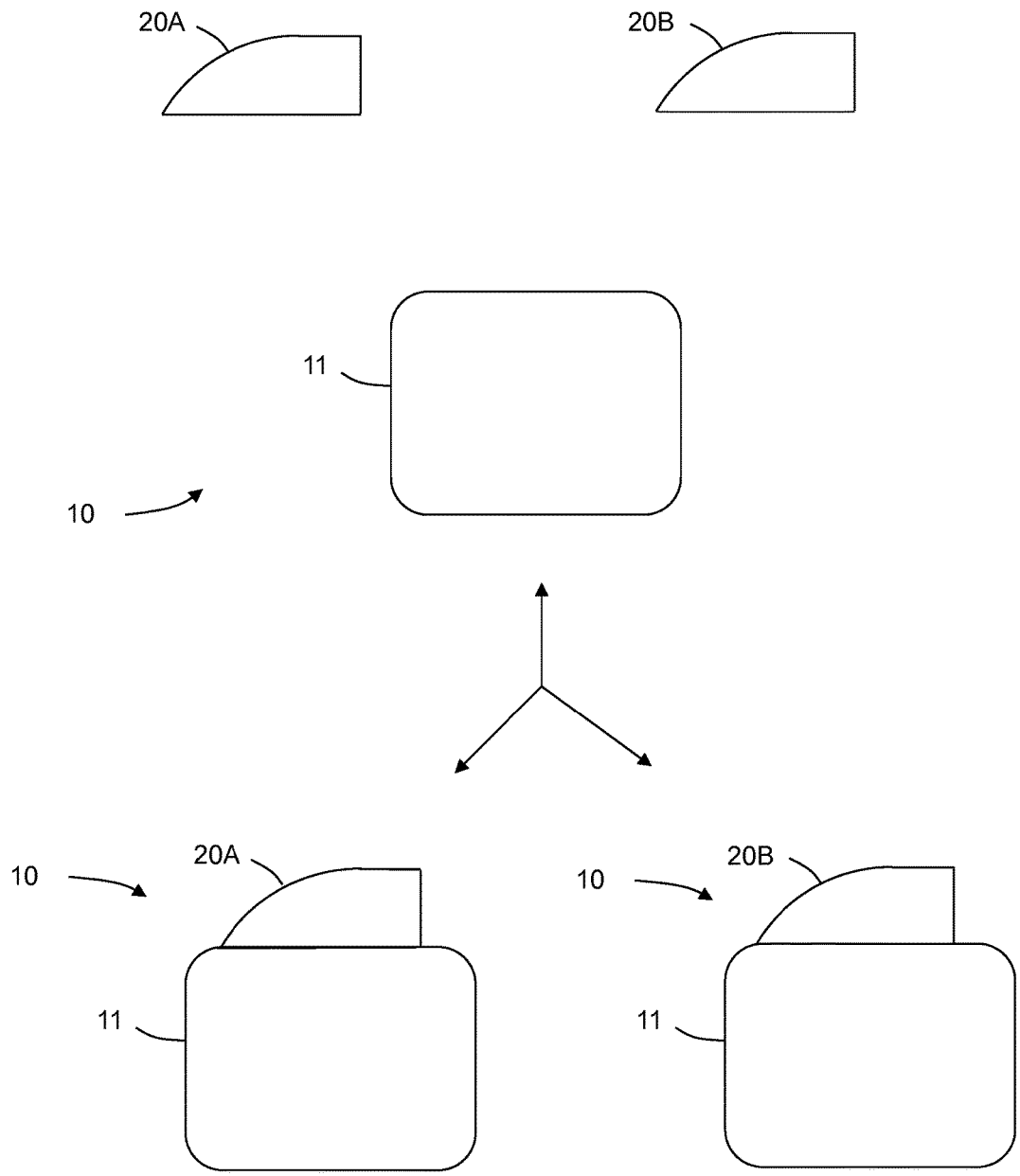
FIG. 5 is a schematic diagram of a system having a device body portion and swappable headers for forming an implantable medical electrical device.
Figure 6:
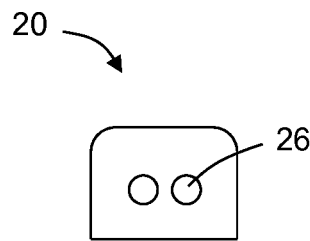
FIGS. 6-8 are schematic front views of swappable headers having different receptacle configurations.
Figure 7:
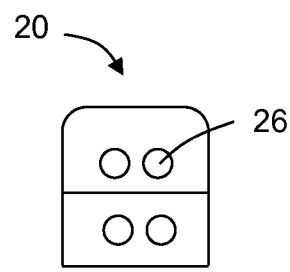
Figure 8:
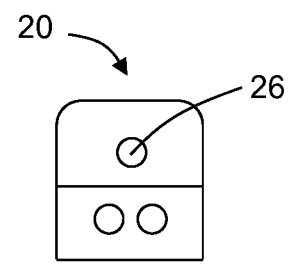

Another way to achieve flexibility in the types of leads that may be employed with an implantable electrical medical device is depicted in FIGS. 5-9. The medical device 10 has a housing 11 in which electronics (not shown) are disposed. Swappable headers 20A, 20B may be coupled to, or removed from, the housing 11 such that internal contacts of the receptacles 26 of the headers 20 are electrically coupled to channels of the electronics. As shown in FIGS. 6-8, the swappable headers may have any suitable number of receptacles 26, each having any suitable number of internal contacts.

For example, if the device depicted in FIG. 5 has 16 channels, the swappable headers 20 depicted in FIGS. 6-8 may have receptacles configured as follows: the header 20 of FIG. 6 may have two receptacles 26, each having eight contacts (to accept a lead having eight contacts and eight electrodes), the header 20 of FIG. 7 may have four receptacles 26 with each having four contacts; and the header 20 of FIG. 8 may have three receptacles 26, with one having eight contacts and two having four contacts.

With swappable headers, a physician or other healthcare provider may select a header that allows for connection with desired leads. Thus, a physician should be able to select a header such that there are no unused receptacles 26. However, if there may be unused receptacles, it may be desirable to factory seal or plug the unused receptacles to prevent bodily fluid from entering the unused receptacles and causing pocket stimulation. In addition or alternatively, the receptacles may include a switch that activates the circuitry to the contacts when the lead is inserted in the receptacle, a fuse that blows when the device is activated and a lead is not present in the receptacle, or the like. Examples of seals, plugs, fuses, switches, and the like are described in U.S. patent application Ser. No. 13/298,386, entitled VARYING LEAD CONFIGURATION IMPLANTABLE MEDICAL DEVICE, filed on Nov. 17, 2011, now issued as U.S. Pat. No. 9,522,281 on Dec. 20, 2016, which application is hereby incorporated herein by reference to the extent that it does not conflict with the disclosure presented herein.

Figure 9:
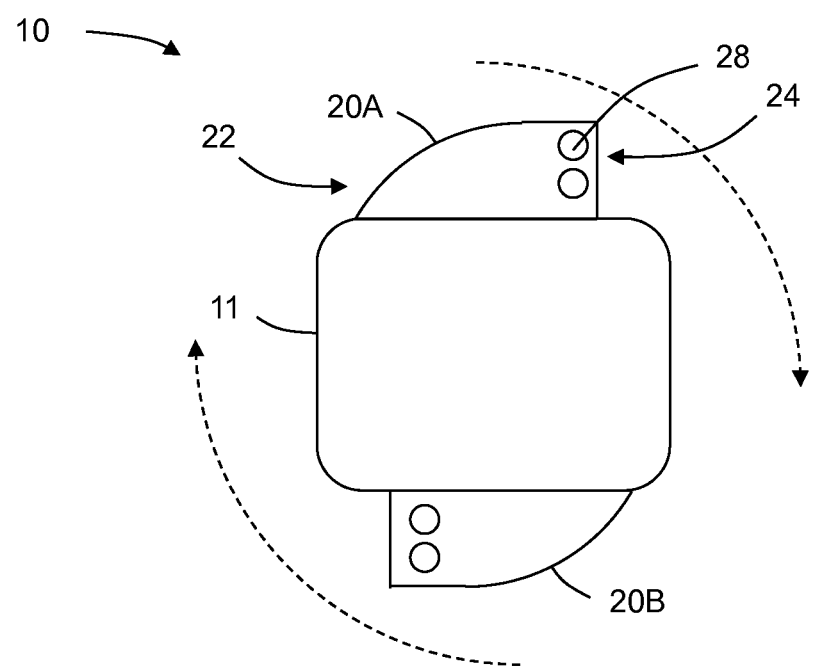
FIG. 9 is a schematic side view of an implantable electrical medical device having two connector headers.
Figure 10:
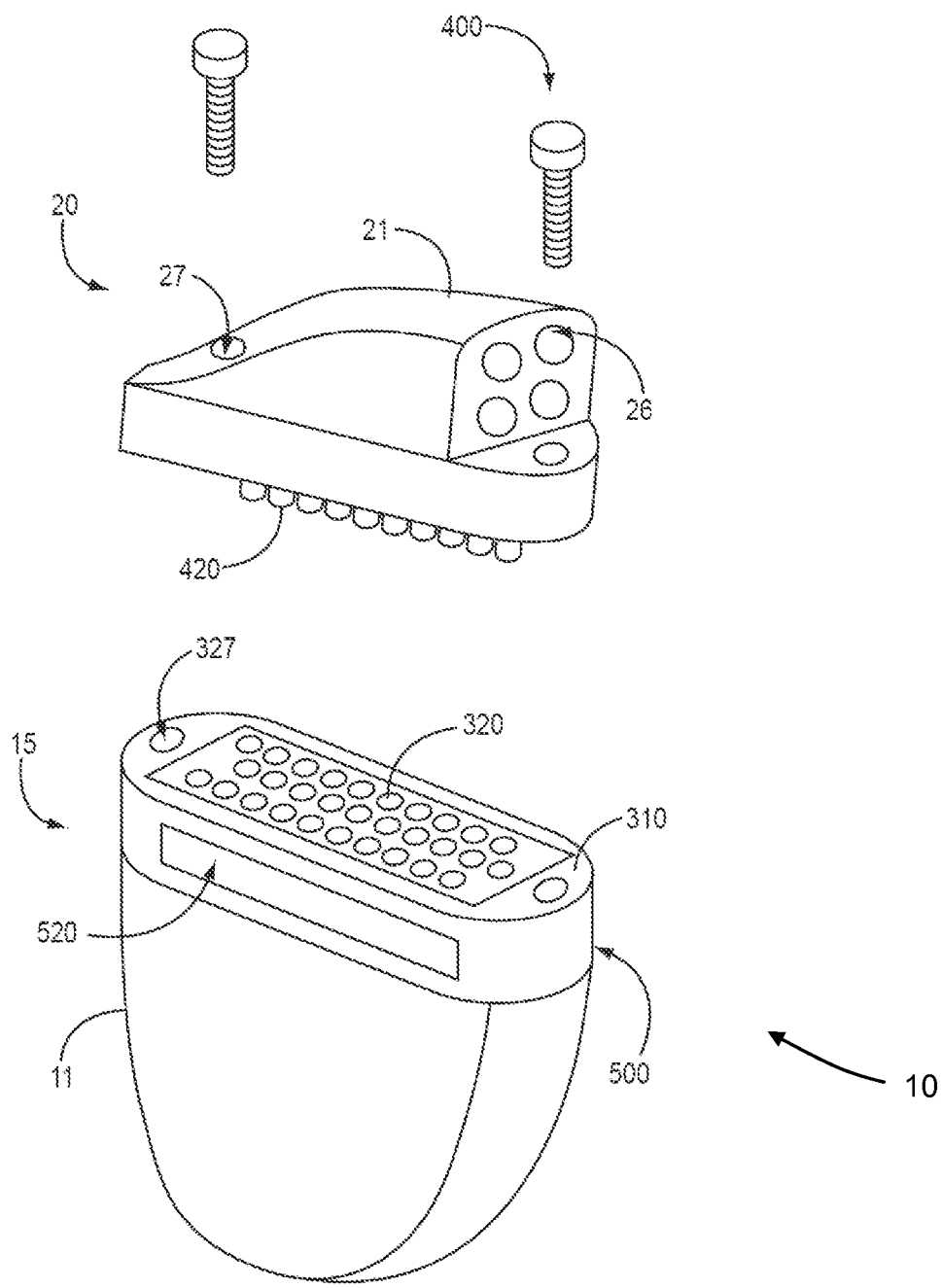
FIG. 10 is a schematic perspective view of an embodiment of an electrical medical device having a connector header and a device body portion.

As shown in FIG. 9, an implantable electrical medical device 10 may include two (or more) header blocks 20A, 20B in which one or more are swappable. This can add even more flexibility to a physician or healthcare provider for using a combination of leads that they deem desirable for a given therapy or therapies. Note that the headers 20A, 20B may be arranged such that they are both oriented in a clockwise (or counter clockwise manner). That is the headers 20A, 20B are arranged such that the orientation from back 22 to front 24 of each of the headers 20 is clockwise around the device 10. Of course, each of the headers 20A, 20B could be oriented in a counter-clockwise manner around the housing. By orienting the headers 20A, 20B in this manner, the leads that extend from the headers may be easily wrapped around the device 10 in the same direction, without all of the leads extending from a single header. While only two headers are shown in FIG. 9, it will be understood that any number of three or four or more headers may be arranged around the housing in a similar manner, with each header being configured to receive any number of leads.

Still referring to FIG. 9, the depicted headers 20A, 20B are configured to each receive two leads. Set screws 28 may be positioned on the side of the header 20A, 20B rather than on the top (e.g., as depicted in FIG. 4C). Thus, the set screws 28 of each of the headers 20A, 20B may be accessible from one side face of the device 10 allowing for loosening or tightening of the screws while the device is in a subcutaneous pocket of a patient.

Regardless of the number of swappable header blocks employed, the blocks are preferably attachable relative to the housing of the device such that a fluid seal prevents access of body fluids to electronic components of the device portion or the header portion through the junction of the attached header portion and device body portion. In embodiments, the header is also detachable such that a different header may be attached by a user, such as an implanting physician, if desired. The swappable headers may be attached to the device body portion in any suitable manner.

For example and with reference to FIGS. 10-18, an embodiment of a system 10, or portions or components thereof, including header 20 attachable to a body portion 15 of an implantable electrical medical device is shown. The device body portion 15 includes a plurality of device contacts 320 electrically coupled to feedthroughs 12 (FIG. 11) extending through hermetically sealed housing 11. In embodiments, each contact 320 is electrically coupled to a discrete feedthrough 12 as depicted, which is coupled to a discrete channel of the electronics of the device. The contacts 320 are spaced apart in a predetermined manner or pattern such that contacts 420 of header 20 electrically couple with contacts 320 of device body portion 15 when the header 20 is operably secured relative to the device body portion 15. Any number of contacts 320 may be included, and contacts 320 may be arranged in any desired manner using any pattern and/or spacing so long as contacts 420 of header 20 are arranged to make electrical contact with contacts 320.

Still with reference to FIGS. 10-18, the header contacts 420 are electrically coupled to internal contacts 23 (FIG. 12) of receptacle 26. Accordingly, when header 20 is appropriately secured relative to body portion 15, the internal contacts 23 of the lead receptacles 26 may be electrically coupled to discrete channels of the electronics of the device because the internal contacts 23 are coupled to the header contacts 420, which are coupled to the device contacts 320, which are coupled to the feedthroughs 12, which are coupled to channels of the device electronics.

The header 20 may be coupled to the device body portion 15 in any suitable manner. For example, one or more mechanical fasteners 400 may be used. In the embodiment depicted in FIG. 10, the header housing 21 forms bores 27, through which a portion of a mechanical fastener 400, such as a screw or bolt, may be advanced. The device body portion 15 includes bores 327 through which a portion of the mechanical fastener may advance. The body bores 327 are positioned such that they align with bores 27 of header 20 when the header is operably secured relative to body portion 15. The mechanical fasteners 400 may be advanced through bores 27, 327 to secure header 20 relative to body portion 15. If the mechanical fasteners 400 are screws, bolts or the like, bores 327 may be threaded to engage the bolt or screw and tighten the header 20 relative to body portion 15 when the fastener 400 is advanced into bore 327.

In embodiments (not shown), the header 20 is coupleable to the device body portion 15 via a snap fit mechanism, wherein the header 20 and the body portion 15 have complementary snap fit elements that allow the header 20 to be secured relative to the body portion 15 by pressing the header 20 against the body portion 15 until the header snaps into place.

Figure 11:
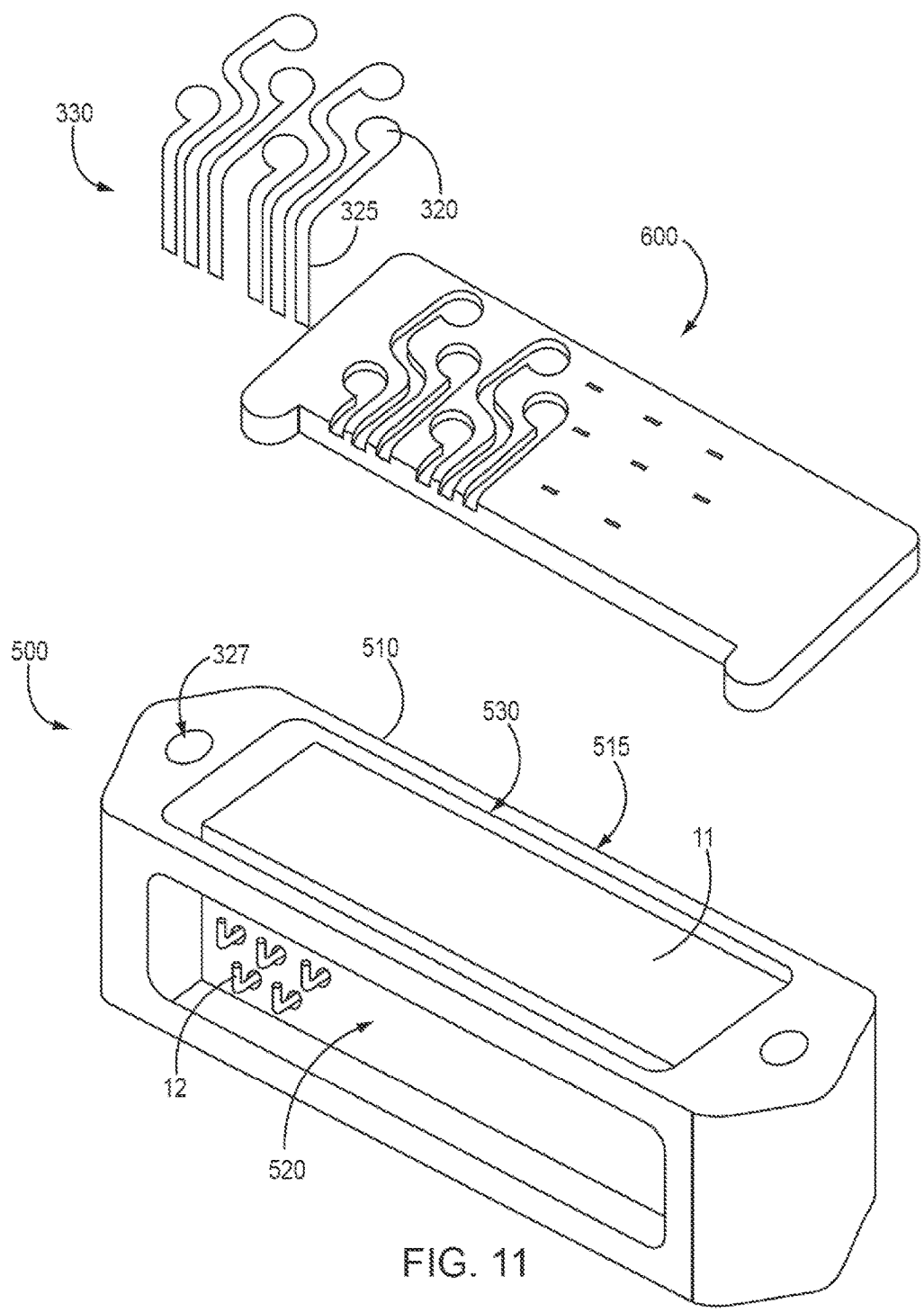
FIG. 11 is a schematic perspective view showing a portion of the device body portion, and components thereof, of an embodiment of the device depicted in FIG. 10.

Referring now specifically to FIG. 11, the device body portion may include a frame assembly 500 mounted around a portion of the hermetically sealed housing 11 of the device through which feedthroughs 12 are extended. The frame 500 may be attached to the device housing 11 in any suitable manner, such as by welding, adhesive, fastener or the like. The frame 500 has a body 510 forming a side window 520 through which feedthroughs 12 are accessible. Conductive contacts 320 may be electrically coupled to feedthroughs 12 by welding, brazing or soldering conductive extensions 325, which extend from contact pads 320, to feedthroughs 12. The contacts 320 and extensions 325 may be part of a one-piece contact frame assembly 330, such as those described in, for example, U.S. Pat. No. 7,537,474, entitled LEAD RECEPTACLE AND PIN FRAME ASSEMBLY and assigned to Medtronic, Inc., which patent is hereby incorporated herein by reference to the extent that it does not conflict with the disclosure presented herein.

While FIG. 11 depicts bent feedthroughs 12 and extensions 325, it will be understood that the feedthroughs 12 may be operably coupled to contacts 320 in any suitable manner. In embodiments (not shown), straight feedthroughs extend through the top of housing 11 and fit into a hole of straight extensions to make electrical contact. Other mechanisms for electrically coupling feedthroughs to contacts are known in the art and may be readily applied.

Prior to coupling the extensions 325 to feedthroughs 12, the contact pads 320 and a portion of the extensions 325 may be placed in detents of insulating pad 600, the top of which may be positioned at or below the level of top window 530 of frame body 510. The pad 600 may rest on top of housing 11 underneath the top window 530 of frame 500. Regardless of the position of the pad 600 and contacts 320, the contacts 320 are preferably accessible and electrically couplable to corresponding header contacts when the header is coupled to the frame 500, e.g. via threaded bores 327 formed in the body 510 of the frame.

After coupling the extensions 325 to feedthroughs 12, the interior of the frame 500 may be backfilled or over-molded with insulating polymer, such as liquid silicone rubber or the like, to insulate the contacts 320, extensions 325 and feedthroughs 12 from each other and from body fluid when the device in implanted in a patients, provided that contacts 320 are electrically accessible to the contacts of the header.

The electrically insulating pad 600 may serve to provide support for contacts 320 such that when the corresponding contacts of the header are pressed against contacts 320, the pad 600 prevents or inhibits contacts 320 from moving away from the header contacts (essentially causing contacts 320 to press back against the header contacts) to ensure good electrical connection between contacts 320 and header contacts.

The insulating pad 600 may also facilitate electrical isolation of individual contacts 320 from other one another. The detents 610 may aid in such electrical isolation by surrounding the contacts 320 and extensions 325 on the bottom and sides of the contacts and extensions, leaving the contacts and extensions exposed only on one surface.

The insulating pad 600 may be made from any suitable material or materials. For example, the insulating pad may be formed from an electrically insulating polymeric material, such as silicone, polystyrene, or the like. In embodiments, the insulating pad 600 is formed from a fabric mesh and a polymer layer, such as a polymer layer over a fabric mesh or a fabric mesh over a polymer layer.

Figure 12:
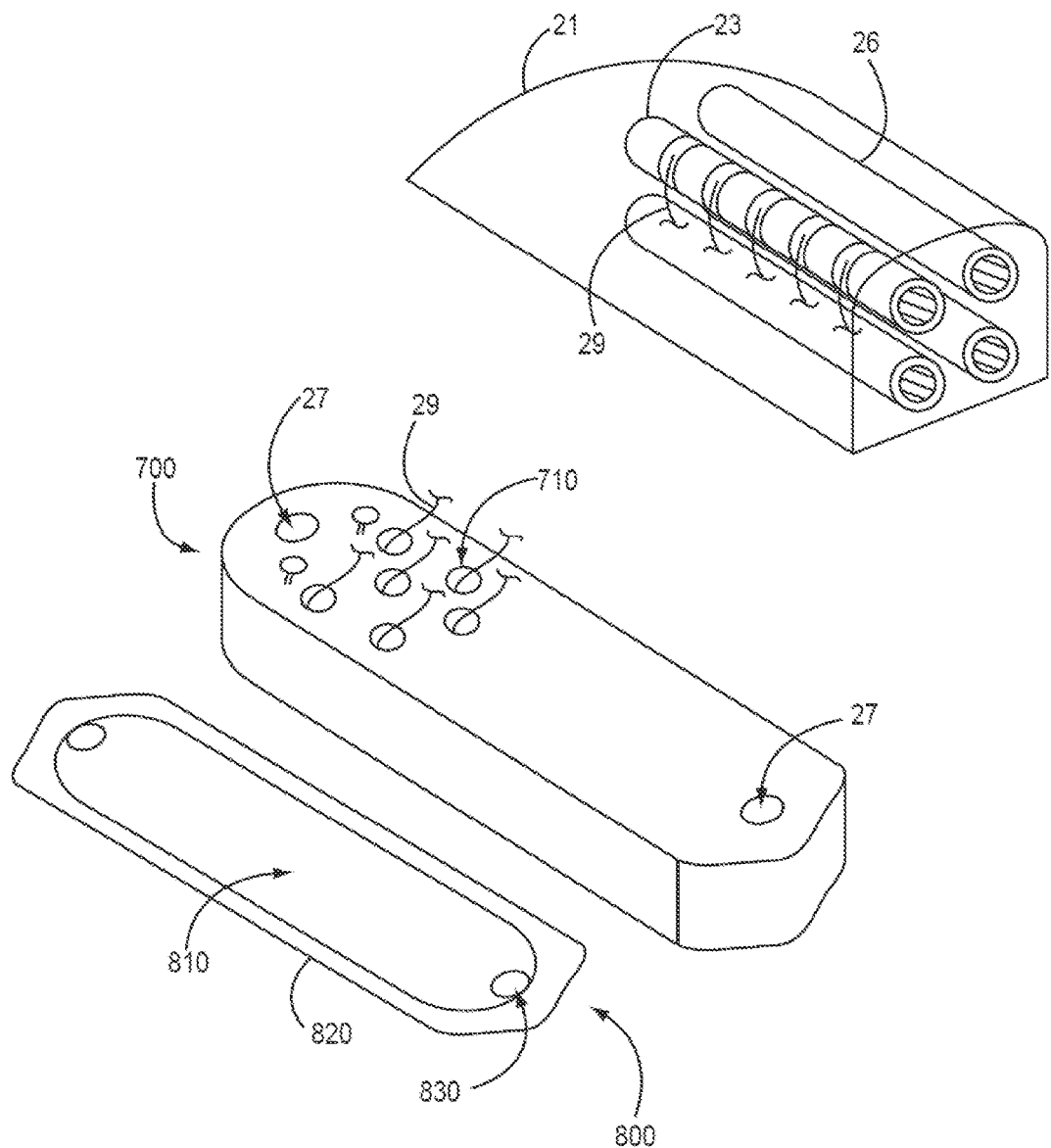
FIG. 12 is a schematic perspective view showing components of a header portion of an embodiment of the device depicted in FIG. 10 and a gasket.

Referring now to FIG. 12, components of an embodiment of a connector header and a gasket 800 are shown. The connector header includes a header housing 21, which may be similar to thermoplastic or elastomeric polymeric header housings used on currently available implantable electrical devices. The housing 21 has openings in a front face in communication with lead receptacles 26 disposed in the housing 21. The receptacles 26 have internal contacts 23 configured to operably couple with contacts of leads when the leads are inserted into the receptacles 26. The receptacle contacts 23 are electrically coupled to header contacts via conductors 29, such as wires or extensions of one-piece contact assemblies as discussed above with regard to the device contacts (see e.g., discussion with regard to FIG. 11 above). The header contacts (not shown in FIG. 12) may be disposed on or project from the under surface of the header plate 700. As shown in FIG. 12, the header plate 700 may have a plurality of bores or openings 710 through which the conductive elements 29 may run to connect to contacts. Alternatively, the contacts may extend through the bores or openings 710 and conductors 29 may be electrically coupled, e.g. welded or soldered, to contacts on upper side of plate 710.

In embodiments, once the receptacle contacts 23 are operably coupled to the header contacts, the header assembly may be over-molded or the header may be backfilled with insulating polymer to seal receptacles, contacts, conductors and the for purposes of electrical isolation and to seal from body fluid when implanted.

The header plate 700 may be formed from any suitable material. In embodiments, the header plate 700 is formed from a metallic material, such as stainless steel or titanium, to provide suitable strength for tightening the header to the body portion of the device via a mechanical fastener. In embodiments, an insulating polymeric material is molded over a metallic support to form header plate component. In embodiments, the header plate is formed of polymeric material. In embodiments, the header frame and housing 21 are formed of the same polymeric material and are formed as one unit. In embodiments, the header housing 21 is attached, fastened or adhered or otherwise secured to the header plate 700.

A gasket 800, such as a silicone gasket, may be disposed between header plate 700 and body portion of device to aid in forming a fluid seal between the body portion and the header when the header is secured relative to the body portion. The gasket 800 may include a central opening 810 to allow header contacts to couple with device body portion contacts when the header is secured relative to the body portion. The gasket 800 is thus configured to prevent body fluids from entering the interface between the header and the device body portion when the device is implanted in a subject, while allowing electrical connection between the contacts of the header and the contacts of the device body portion. As shown in FIG. 12, the gasket 800 may have a continuous edge portion 820 in which openings 830 are formed. The openings 830 are configured to receive and allow passage of mechanical fasteners therethrough.

Figure 13:
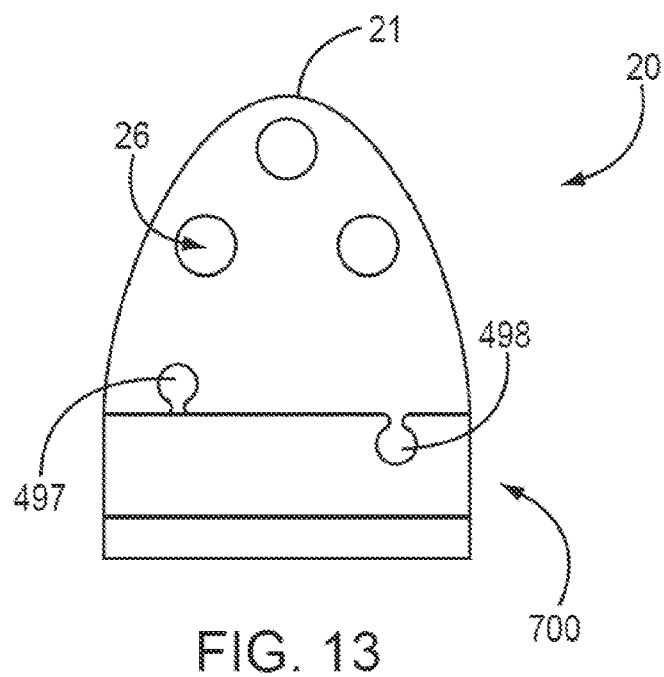
FIG. 13 is a schematic sectional view of an embodiment of a header of an embodiment of the device depicted in FIG. 10.
Figure 14:
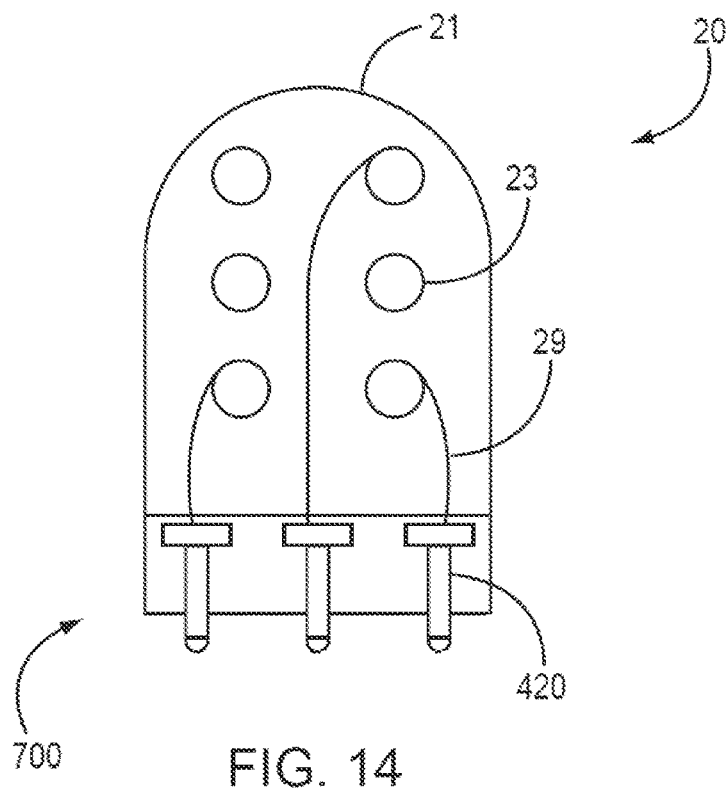
FIG. 14 is a schematic sectional view of an embodiment of a header of an embodiment of the device depicted in FIG. 10.

Referring now to FIGS. 13-14, different views of header 20 are shown. In the view depicted in FIG. 13, mechanical interlocks 497, 498 are shown. The interlocks 497, 498 are depicted as complementary posts 497 and cavities 498 although many other types of complementary mating features are contemplated herein and may be readily employed by those skilled in the art. The housing 21 and plate 700 include complementary interlock features 497, 498 that are configured to be aligned and to retain relative position of the plate 700 and housing 21. The mechanical interlocks 497, 498 retain the position of the plate 700 and housing 21 after an over-molding process. The over-molding process may serve to seal the housing 21 onto the plate 700 to provide electrical isolation and sealing against intrusion of body fluid when implanted. Of course, the housing 21 and the plate 700 may be connected in any suitable manner, such as through mechanical fasteners that hold header to device body portion, adhesive, welding, or the like.

In FIG. 14, header contacts 420 are electrically coupled to receptacle contacts 23 via conductors 29. The contacts 420 may be spring loaded contacts, such as pogo pin contacts. The contacts 420 extend through at least a portion of openings or bores (see, e.g., 710 in FIG. 12) in the plate 700. Securing of the housing 21 to the plate 700 applies pressure to the top portion of the pins 420, preventing or inhibiting the top portion of the contact pin 420 from moving upward into the header 21 portion when the header 20 is secured relative to the device body portion. In embodiments, the housing 21 is secured to the plate 700 via overmolding the housing 21, as a part of forming the housing, onto the plate 700.

The contacts 420, or portions thereof, may be made of any suitable conductive material, such as a metallic conductive material, to conduct electricity from the point of contact with conductor 29 to the tip of the contact on the bottom side of plate 700 where the contacts 420 will electrically couple with device contacts. In embodiments, the contacts 420, or portions thereof, are insulated with a polymeric material in the form of, e.g., a coating or sleeve, which can be advantageous when the plate 700 is metallic or has a metallic or conductive surface that may interact with contact 420. The insulating polymer can serve to electrically isolate the contacts 420.

Figure 15:
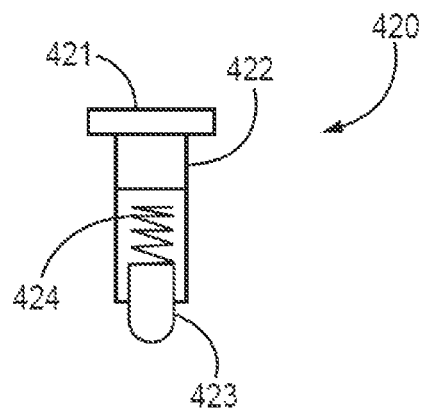
FIG. 15 is a schematic side view of an embodiment of a contact pin that may be used in an embodiment of a header.

Referring now to FIG. 15, an embodiment of a spring loaded contact 420 that may be employed in accordance with the teachings presented herein is shown. The contact 420 is a pogo pin-type contact and has a top flanged portion 421 transverse to an extending body portion 422. The top flanged portion 421 has a larger outer diameter than the extending body portion 422. The outer diameter of the body portion 422 is smaller than the smallest inner diameter of a bore in the header plate. However, the outer diameter of the flanged top portion 421 is larger than the smallest inner diameter of the bore in the header plate to prevent the contact from falling through the bore. The contact 420 includes an electrically conductive tip portion 423 that longitudinally extends away from the body 422. The tip 423 is biased in a fully extended position by spring element 424, but may retract into body 422 upon application of upward force on tip 423. The spring element 424 serves to press conductive tip 423 of contact 424 against a corresponding contact of device body portion (see, e.g. contact 320 of FIG. 10) when the header is attached to the device body portion.

Figure 16:
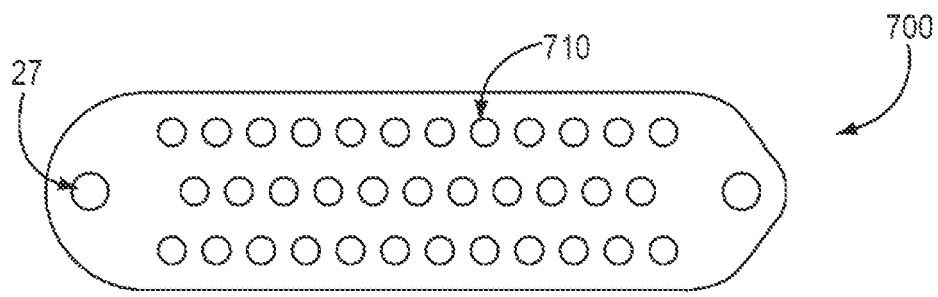
FIG. 16 is a schematic top view of an embodiment of a header plate.

Referring now to FIG. 16, a schematic top view of a connector plate 700 is shown. Openings 710 or bores are shown extending through the bottom major surface of plate 700. The openings of the bores 710 in the plate 700 are configured to align with the contacts of the device body portion (e.g., contacts 320 in FIG. 10) when the header is secured relative to the device body portion.

Figure 17:
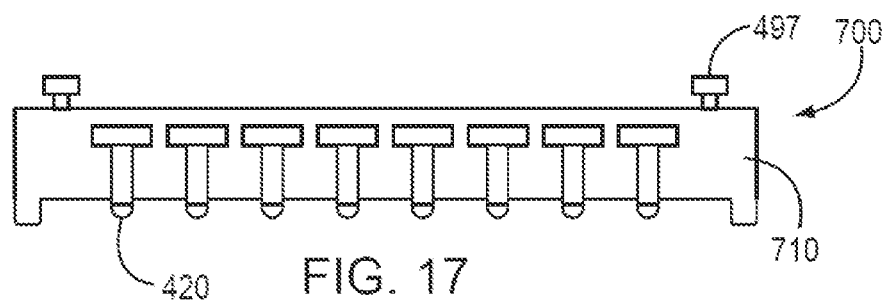
FIG. 17 is a schematic sectional view of an embodiment of a header plate showing contact pins disposed in bores of the plate.

Referring now to FIG. 17, a schematic sectional view of the plate 700 depicted in FIG. 16 is shown, with contact pins 420 shown disposed in the bores. The plate 700 includes mechanical interlock elements 497 configured to align and secure the plate 700 relative to the header housing. The header housing is preferably mechanically interlocked and sealed with plate 700 during manufacture.

Figure 18:
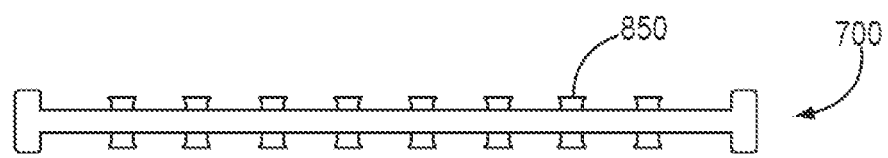
FIG. 18 is a schematic side view of an embodiment of a gasket.

As shown in FIG. 18, gasket 800 may include a plurality of sealing features 850 configures to sealingly engage a portion of contact pin disposed through the gasket to individually seal the contact pins. It is worth noting that this is in contrast to the gasket 800 depicted in FIG. 12 which has a large central window 810. Either type of gasket (e.g., one as shown in FIG. 18 or one shown in FIG. 12), or components or features thereof, may be employed in the various embodiments described herein.

While the devices depicted in FIGS. 10-18 have only one swappable header, embodiments of such devices may include more than one swappable header (see, e.g., FIG. 9).

It will be understood that combinations of the various embodiments described herein, or portions or components thereof, are contemplated.

The present disclosure describes a variety of implantable infusion devices. A summary of some selected aspects of such devices is provided below.

In a first aspect, an implantable electrical medical system includes a device body portion comprising (i) a hermetically sealed housing; (ii) electronics disposed in the housing and configured to generate or receive an electrical signal, the electronics containing a plurality of channels through which the electrical signal may be transmitted; (iii) electronics disposed in the housing and configured to generate or receive an electrical signal, the electronics containing a plurality of channels through which the electrical signal may be transmitted; (iv) a plurality of feedthroughs extending through the hermetically sealed housing, wherein each feedthrough is operably coupled to a discrete channel of the electronics; and (v) a plurality of device contacts electrically coupled to the feedthroughs, wherein each device contact is electrically coupled to a discrete feedthrough. The system further includes a first connector header portion comprising (i) a housing defining a bore; (ii) a lead receptacle within the bore of the housing; the lead receptacle comprising a plurality of receptacle contacts operably couplable to a lead inserted into the receptacle; and (iii) a plurality of header contacts electrically coupled to the receptacle contacts, wherein each of the header contacts is electrically coupled to a discrete receptacle contact. The first connector header portion is removable from and attachable to the device body portion such that, when attached, the header contacts and the device contacts electrically couple.

A second aspect is a system of the first aspect, wherein the device body portion further comprises an electrically insulating pad having a major surface, wherein the device contacts are exposed through or disposed on the major surface of the insulating pad.

A third aspect is a system of the second aspect, wherein the connector header portion comprises a plate having a major surface, wherein the header contacts are exposed through or disposed on the major surface of the plate.

A fourth aspect is a system of the third aspect, wherein the header contacts comprise spring loaded pins extending beyond the major surface of the plate of the connector header portion.

A fifth aspect is a system of the third or fourth aspect, wherein the major surface of the insulating pad of the device body portion faces the major surface of the plate of the connector header portion when the connector header portion is attached to the device body portion.

A sixth aspect is a system of any of aspects 3-5, further comprising a gasket between the insulating pad of the device body portion and the plate of the connector header portion when the connector header portion is attached to the device body portion.

A seventh aspect is a system of aspect 1 or 2, further comprising a gasket disposed between the connector header portion and the device body portion when the connector header portion is attached to the device body portion.

An eighth aspect is a system of any of aspects claims 1-7, wherein the connector header portion is removable and attachable to the device body portion via one or more threaded fastener.

A ninth aspect is a system of any of aspects 1-8, wherein the device body portion comprises a side window filled with an insulating polymer, wherein the feedthroughs are accessible through the side window prior to filling with polymer.

A tenth aspect is a system of the ninth aspect, wherein the side window is configured to allow access to electrically connect the device contacts to the feedthroughs.

An eleventh aspect is a system of the ninth aspect, wherein the side window is defined by a frame welded to the housing.

A twelfth aspect is a system of any of aspects 1-11, further comprising a second connector header portion, wherein the second connector header portion comprises (i) a housing defining a bore; (ii) a lead receptacle within the bore of the housing, the lead receptacle comprising a plurality of receptacle contacts operably couplable to a lead inserted into the receptacle; and (iii) a plurality of header contacts electrically coupled to the receptacle contacts, wherein each of the header contacts is electrically coupled to a discrete receptacle contact, wherein the second connector header portion is removable and attachable to the device body portion such that, when attached, the header contacts and the device contacts electrically couple.

A thirteenth aspect is a system of the twelfth aspect, wherein the lead receptacle of the second connector header is configured to receive a lead different from a lead which the lead receptacle of the first connector header is configured to receive.

A fourteenth aspect is a system of the thirteenth aspect, wherein the lead receptacle of the second connector header is configured to receive a lead with the same number on proximal contacts as the lead which the lead receptacle of the first connector header is configured to receive, wherein the spacing of the proximal contacts of the lead that the lead receptacle of the second connector header is configured to receive is different from the spacing of the proximal contacts of the lead that the lead receptacle of the first connector header is configured to receive.

In a fifteenth aspect, an implantable electrical medical system includes a device body portion comprising (i) a hermetically sealed housing; (ii) electronics disposed in the housing and configured to generate or receive an electrical signal, the electronics containing a plurality of channels through which the electrical signal may be transmitted; (iii) a first set of a plurality of feedthroughs extending through the hermetically sealed housing, wherein each feedthrough is operably coupled to a discrete channel of the electronics; (iv) a second set of a plurality of feedthroughs extending through the hermetically sealed housing, wherein each feedthrough is operably coupled to a discrete channel of the electronics; (vi) a first set of a plurality of device contacts electrically coupled to the first set of feedthroughs, wherein each device contact is electrically coupled to a discrete feedthrough; and (vii) a second set of a plurality of device contacts electrically coupled to the second set of feedthroughs, wherein each device contact is electrically coupled to a discrete feedthrough. The system further includes a first connector header portion comprising (i) a housing defining a bore; (ii) a lead receptacle within the bore of the housing; the lead receptacle comprising a plurality of receptacle contacts operably couplable to a lead inserted into the receptacle; and (iii) a plurality of header contacts electrically coupled to the receptacle contacts, wherein each of the header contacts is electrically coupled to a discrete receptacle contact, wherein the first connector header portion is removable and attachable to the device body portion such that, when attached, the first header contacts and the first set of device contacts electrically couple. The system further includes a second connector header portion comprising (i) a housing defining a bore; (ii) a lead receptacle within the bore of the housing; the lead receptacle comprising a plurality of receptacle contacts operably couplable to a lead inserted into the receptacle; and (iii) a plurality of second header contacts electrically coupled to the receptacle contacts, wherein each of the header contacts is electrically coupled to a discrete receptacle contact, wherein the second connector header portion is removable and attachable to the device body portion such that, when attached, the second header contacts and the second set of device contacts electrically couple.

A sixteenth aspect is a system of the fifteenth aspect, wherein the first connector header portion has a back and a front face, wherein the front face defines an opening in communication with the bore; wherein the second connector header portion has a back and a front face, wherein the front face defines an opening in communication with the bore; and wherein the first and second connector header portions, when attached to the device body portion, are arranged such that the orientation from front to back of each of the first and second connector header portions is clockwise or counterclockwise around the housing of the device body portion.

A seventeenth aspect is a system of the fifteenth or sixteenth aspect, wherein the device body portion further comprises (i) a first electrically insulating pad having a major surface, wherein the first set of device contacts are exposed through or disposed on the major surface of the first pad; and (ii) a second electrically insulating pad having a major surface, wherein the second set of device contacts are exposed through or disposed on the major surface of the second pad.

An eighteenth aspect is a system of the seventeenth aspect, wherein the first connector header portion comprises a first plate having a major surface, wherein the first header contacts are exposed through or disposed on the major surface of the first plate, and wherein the second connector header portion comprises a second plate having a major surface, wherein the second header contacts are exposed through or disposed on the major surface of the second plate.

A nineteenth aspect is as system of the eighteenth aspect, wherein the first header contacts comprise spring loaded pins extending beyond the major surface of the first plate of the first connector header portion, and wherein the second header contacts comprise spring loaded pins extending beyond the major surface of the second plate of the second connector header portion.

A twentieth aspect is a system of the eighteenth or nineteenth aspect, wherein the major surface of the first insulating pad of the device body portion faces the major surface of the first plate of the first connector header portion when the first connector header portion is attached to the device body portion, and wherein the major surface of the second insulating pad of the device body portion faces the major surface of the second plate of the second connector header portion when the second connector header portion is attached to the device body portion.

A twenty-first aspect is a system of any of aspects 18-20, further comprising (i) a first gasket between the first insulating pad of the device body portion and the first plate of the first connector header portion when the first connector header portion is attached to the device body portion; and (ii) a second gasket between the second insulating pad of the device body portion and the second plate of the second connector header portion when the second connector header portion is attached to the device body portion.

A twenty-second aspect is a system of any of aspects 15-17, further comprising a first gasket disposed between the first connector header portion and the device body portion when the first connector header portion is attached to the device body portion; and a second gasket disposed between the second connector header portion and the device body portion when the second connector header portion is attached to the device body portion.

A twenty-third aspect is a system of any of aspects 15-22, wherein the first and second connector header portions are removable and attachable to the device body portion via threaded fasteners.

A twenty-fourth aspect is a system of any of aspects 15-23, wherein the device body portion comprises a first side window filled with an insulating polymer, wherein the first feedthroughs are accessible through the first side window prior to filling with polymer; and a second side window filled with an insulating polymer, wherein the second feedthroughs are accessible through the second side window prior to filling with polymer.

A twenty-fifth aspect is a system of aspect 24, wherein the first and second side windows are configured to allow access to electrically connect the device contacts to the feedthroughs.

A twenty-sixth aspect is a system of aspect 25, wherein the first side window is defined by a first frame welded to the housing and wherein the second side window is defined by a second frame welded to the housing.

A twenty-seventh aspects is a system of any of aspects 15-26, further comprising a third connector header portion, wherein the third connector header portion comprises (i) a housing defining a bore; (ii) a lead receptacle within the bore of the housing; the lead receptacle comprising a plurality of receptacle contacts operably couplable to a lead inserted into the receptacle; and (iii) a plurality of header contacts electrically coupled to the receptacle contacts, wherein each of the header contacts is electrically coupled to a discrete receptacle contact, and wherein the header contacts are spaced apart in a predetermined manner, wherein the third connector header portion is removable and attachable to the device body portion such that, when attached, the header contacts and the first or second set of device contacts electrically couple.

A twenty-eighth aspect is a system of the twenty-seventh aspect, wherein the lead receptacle of the third connector header is configured to receive a lead different from a lead which the lead receptacle of the first connector header or the lead receptacle of the second connector header is configured to receive.

In a twenty-ninth aspect, a method for manufacturing a device body portion of an implantable medical device, wherein the device body portion is configured to receive a plurality of connector header portions, includes (i) providing a device body portion having a hermetically sealed housing, electronics disposed in the housing and having a plurality of channels through which electrical signals may be transmitted and a plurality of feedthroughs extending through the hermetically sealed housing, wherein each feedthrough is operably coupled to a discrete channel of the electronics; (ii) welding a frame on the housing of the device body portion over the feedthroughs, wherein the frame has a side window through which the feedthroughs are accessible; (iii) electrically coupling contact pads to the feedthroughs such that each contact pad is discretely coupled to a feedthrough; and filling the side window of the frame with an electrically insulating polymer.

In a thirtieth aspect, an implantable electrical medical device configured to be coupleable to a swappable header configured to receive one or more leads and to operably couple the leads to the device, includes (i) a hermetically sealed housing; (ii) electronics disposed in the housing and configured to generate or receive an electrical signal, the electronics containing a plurality of channels through which the electrical signal may be transmitted; (iii) a plurality of feedthroughs extending through the hermetically sealed housing, wherein each feedthrough is operably coupled to a discrete channel of the electronics; and (iv) a plurality of contacts electrically coupled to the feedthroughs, wherein each contact is electrically coupled to a discrete feedthrough, wherein the contacts are positioned such that proper alignment and attachment of the swappable header to the device causes the contacts to be electrically coupled to corresponding contacts of the header such that leads inserted into the header may be operably coupled to the electronics of the device via the contacts of the header, the contacts of the device, and the feedthroughs.

A thirty-first aspect is a device of the thirtieth aspect, further comprising an electrically insulating pad having a major surface, wherein the contacts are exposed through or disposed on the major surface of the insulating pad.

Thus, embodiments of the IMPLANTABLE MEDICAL DEVICE WITH SWAPPABLE HEADERS are disclosed. One skilled in the art will appreciate that the present invention can be practiced with embodiments other than those disclosed. The disclosed embodiments are presented for purposes of illustration and not limitation.

What is claimed is:

1. An implantable electrical medical system, comprising:
    a device body portion, comprising:
        a hermetically sealed housing;
        electronics disposed in the housing and configured to generate or receive an electrical signal, the electronics containing a plurality of channels through which the electrical signal may be transmitted;
        a first set of a plurality of feedthroughs extending through the hermetically sealed housing, wherein each feedthrough is operably coupled to a discrete channel of the electronics;
        a second set of a plurality of feedthroughs extending through the hermetically sealed housing, wherein each feedthrough is operably coupled to a discrete channel of the electronics;
        a first set of a plurality of device contacts electrically coupled to the first set of feedthroughs, wherein each device contact is electrically coupled to a discrete feedthrough; and
        a second set of a plurality of device contacts electrically coupled to the second set of feedthroughs, wherein each device contact is electrically coupled to a discrete feedthrough;
    a first connector header portion, comprising:
        a first connector housing defining a bore;
        a lead receptacle within the bore of the first connector housing; the lead receptacle comprising a plurality of receptacle contacts operably couplable to a lead inserted into the receptacle; and
        a plurality of first header contacts electrically coupled to the receptacle contacts, wherein each of the header contacts is electrically coupled to a discrete receptacle contact,
    wherein the first connector header portion is removable and attachable to the device body portion such that, when attached, the first header contacts and the first set of device contacts electrically couple; and
    a second connector header portion separate from the first header portion, comprising:
        a second connector housing defining a bore;
        a lead receptacle within the bore of the second connector housing; the lead receptacle comprising a plurality of second receptacle contacts operably couplable to a lead inserted into the receptacle; and
        a plurality of second header contacts electrically coupled to the second receptacle contacts wherein each of the second header contacts is electrically coupled to a discrete one of the second receptacle contacts,
    wherein the second connector header portion is removable and attachable to the device body portion such that, when attached, the second header contacts and the second set of device contacts electrically couple.

2. The system of claim 1, wherein the device body portion further comprises:
    a first electrically insulating pad having a major surface, wherein the first set of device contacts are exposed through or disposed on the major surface of the first pad; and
    a second electrically insulating pad having a major surface, wherein the second set of device contacts are exposed through or disposed on the major surface of the second pad.

3. The system of claim 2, wherein the first connector header portion comprises a first plate having a major surface, wherein the first header contacts are exposed through or disposed on the major surface of the first plate, and wherein the second connector header portion comprises a second plate having a major surface, wherein the second header contacts are exposed through or disposed on the major surface of the second plate.

4. The system of claim 3, wherein the first header contacts comprise spring loaded pins extending beyond the major surface of the first plate of the first connector header portion, and wherein the second header contacts comprise spring loaded pins extending beyond the major surface of the second plate of the second connector header portion.

5. The system of claim 3, wherein the major surface of the first insulating pad of the device body portion faces the major surface of the first plate of the first connector header portion when the first connector header portion is attached to the device body portion, and wherein the major surface of the second insulating pad of the device body portion faces the major surface of the second plate of the second connector header portion when the second connector header portion is attached to the device body portion.

6. The system of 3, further comprising:
    a first gasket between the first insulating pad of the device body portion and the first plate of the first connector header portion when the first connector header portion is attached to the device body portion; and
    a second gasket between the second insulating pad of the device body portion and the second plate of the second connector header portion when the second connector header portion is attached to the device body portion.

7. The system of claim 1, further comprising a third connector header portion,
    wherein the third connector header portion comprises
        a housing defining a bore;
        a lead receptacle within the bore of the housing; the lead receptacle comprising a plurality of receptacle contacts operably couplable to a lead inserted into the receptacle; and
        a plurality of header contacts electrically coupled to the receptacle contacts, wherein each of the header contacts is electrically coupled to a discrete receptacle contact, and wherein the header contacts are spaced apart in a predetermined manner, wherein the third connector header portion is removable and attachable to the device body portion such that, when attached, the header contacts and the first or second set of device contacts electrically couple.

8. An implantable electrical medical system, comprising:
a device body portion, comprising:
- a hermetically sealed housing;
- electronics disposed in the housing and configured to generate or receive an electrical signal, the electronics containing a plurality of channels through which the electrical signal may be transmitted;
- a plurality of feedthroughs extending through the hermetically sealed housing, wherein each feedthrough is operably coupled to a discrete channel of the electronics; and
- a plurality of device contacts located external to the hermetically sealed housing and electrically coupled to the feedthroughs, wherein each device contact is electrically coupled to a discrete feedthrough; and a first connector header portion, comprising:
- a first connector housing defining a bore;
- a lead receptacle within the bore of the housing; the lead receptacle comprising a plurality of receptacle contacts operably couplable to a lead inserted into the receptacle; and
- a plurality of header contacts located external to the first connector housing and electrically coupled to the receptacle contacts, wherein each of the header contacts is electrically coupled to a discrete receptacle contact, wherein the first connector housing of the first connector header portion is removable from and attachable to the hermetically sealed housing of the device body portion and the plurality of header contacts are positioned such that attachment of the first connector housing to the hermetically sealed housing results in the header contacts and the device contacts electrically coupling, wherein the device body portion further comprises an electrically insulating pad having a major surface, wherein the device contacts are exposed through or disposed on the major surface of the insulating pad, wherein the connector header portion comprises a plate having a major surface, wherein the header contacts are exposed through or disposed on the major surface of the plate, wherein the header contacts comprise spring loaded pins having a tip portion and a spring, wherein the tip portion is biased by the spring to extend beyond the major surface of the plate of the connector header portion and to press the tip against the device body portion when the header is attached to the device body portion, wherein the major surface of the insulating pad of the device body portion faces the major surface of the plate of the connector header portion when the first connector housing of the first connector header portion is attached to the hermetically sealed housing of the device body portion.

9. The system of claim 8, wherein the first connector housing of the first connector header portion is removable and attachable to the hermetically sealed housing of the device body portion via one or more threaded fasteners.

10. The system of claim 8, further comprising a gasket between the insulating pad of the device body portion and the plate of the connector header portion when the first connector housing of the first connector header portion is attached to the hermetically sealed housing of the device body portion.

* * * * *